United States Patent

Hagiwara et al.

[11] Patent Number: 6,165,467
[45] Date of Patent: *Dec. 26, 2000

[54] STABILIZED HUMAN MONOCLONAL ANTIBODY PREPARATION

[75] Inventors: Hideaki Hagiwara, Takarazuka; Hideo Yuasa; Yasunori Yamamoto, both of Kasai, all of Japan

[73] Assignee: Yoshihide Hagiwara, Hyogo-Ken, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/970,393

[22] Filed: Nov. 14, 1997

Related U.S. Application Data

[62] Continuation of application No. 08/810,885, Mar. 5, 1997, abandoned, which is a continuation of application No. 08/357,262, Dec. 13, 1994, abandoned, which is a continuation of application No. 08/030,146, filed as application No. PCT/JP92/00914, Jul. 17, 1992, abandoned.

[30] Foreign Application Priority Data

Jul. 20, 1991 [JP] Japan .................................. 3-204743

[51] Int. Cl.⁷ .................... C07K 16/30; A61K 39/395
[52] U.S. Cl. .................... 424/155.1; 424/142.1; 424/177.1; 530/388.8; 530/388.15; 530/390.5
[58] Field of Search ............ 530/388.15, 390.5, 530/388.8; 424/155.1, 142.1, 177.1

[56] References Cited

U.S. PATENT DOCUMENTS

| | | | |
|---|---|---|---|
| 4,168,303 | 9/1979 | Nishida et al. | 424/85.8 |
| 4,721,777 | 1/1988 | Uemura et al. | 530/389.1 |
| 4,849,508 | 7/1989 | Magnin et al. | 530/390.5 |

FOREIGN PATENT DOCUMENTS

| | | |
|---|---|---|
| 0410207 | 1/1991 | European Pat. Off. . |
| 53-47515 | 4/1978 | Japan . |
| 562917 | 1/1981 | Japan . |
| 56-127320 | 10/1981 | Japan . |
| 60-248626 | 12/1985 | Japan . |
| 63-88197 | 4/1988 | Japan . |
| 225320 | 9/1988 | Japan . |

OTHER PUBLICATIONS

Hudson, L. et al. (ed), Practical Immunology, 2nd edition, pp. 223–225, 335–336, 1980.
Taomoto et al., Biological Aspects of Brain Tumors, Tabuchi (Ed.), Springer–Verlag, Tokyo, pp. 452–463 (1991).
Kokunai et al., J Neurosurg, vol. 73, pp. 901–908 (1990).
Aotsuka et al., Eur J Cancer Clin Oncol., vol. 24, No. 5 pp. 824–828 (1988).
Hagiwara et al., Mol. Biol. Med., vol. 1, pp. 245–252 (1983).
Borrebaeck, Journal of Immunological Methods, vol. 123, pp. 157–165 (1989).
Waldmann, Science, vol. 252, pp. 1657–1662 (1991).
Osband et al., Immunology Today, vol. 11, No. 6, pp. 193–195 (1990).
Merck Index, 10$^{th}$ Edition, Windholz (Ed.), Merck & Co. Inc., N.J. USA No. 5569.

*Primary Examiner*—David Saunders
*Assistant Examiner*—Amy De Cloux

[57] ABSTRACT

A stabilized human monoclonal antibody preparation containing 1 to 20 mg of D-mannitol per 1 mg of a human monoclonal antibody. This preparation is excellent in stability in a solution state, a freeze drying state and a freezing state, particularly stability against aggregation and precipitation of the human monoclonal antibody at the time of redissolution after freeze drying.

2 Claims, No Drawings

STABILIZED HUMAN MONOCLONAL ANTIBODY PREPARATION

This application is a continuation, of application Ser. No. 08/810,885, filed Mar. 5, 1997, now abandoned, which is a continuation of application Ser. No. 08/357,262, filed Dec. 13, 1994, now abandoned, which is a continuation of application Ser. No. 08/030,146, filed Mar. 18, 1993, now abandoned. This family of applications entered the National Phase in the United States under 35 USC 371 via International Application PCT/JP92/00914, filed Jul. 17, 1992.

TECHNICAL FIELD

This invention relates to a stabilized human monoclonal antibody preparation, and more detailedly, relates to a human monoclonal antibody preparation excellent in stability in a solution state, a freeze drying state and a freezing state, particularly redissolution (restoration) stability after freezing drying.

BACKGROUND ART

Since a process for producing a monoclonal antibody by genetic engineering was proposed in 1975 by Koehler and Milstein [Koehler, G., Milstein, C, Nature 256, 495 (1975)], a road has been opened up to supply a large quantity of a monoclonal antibody as a homogeneous antibody, and such monoclonal antibodies have widely been utilized in the medical and biological fields.

Recently, human monoclonal antibodies are provided in human clinical tests, and particularly draw attention in the antitumor-directed medicinal field. However, purified human monoclonal antibodies have an undesirable property as a preparation that they easily aggregate and precipitate in a solution state or at the time of redissolution (restoration) after freeze drying, and development of monoclonal antibody preparations lacking such an undesirable property and being stabilized is desired.

On the other hand, as methods for stabilization of antibodies (immunoglobulins), there have hitherto been proposed a method which comprises adding to a sulfonated immunoglobulin serum albumin, or serum albumin with glycine and/or mannitol (Japanese Patent Publication No. 20965/1987); a method which comprises adding a comparatively large quantity of a polyhydric alcohol (Japanese Laid-Open Patent Publication No. 88197/1988); a method which comprises adding dextran (Japanese Laid-Open Patent Publication No. 225320/1988); etc. However, it is impossible, by these so far proposed methods, to improve sufficiently the above undesirable property in human monoclonal antibody preparations.

The present inventors now found that stability of a human monoclonal antibody preparation, particularly stability against aggregation and precipitation at the time of redissolution after freeze drying of the human monoclonal antibody is remarkably enhanced by compounding a specified small quantity of mannitol to the human monoclonal antibody, and completed this invention.

DISCLOSURE OF INVENTION

Thus, there is provided according to this invention a stabilized human monoclonal antibody preparation containing 1 to 20 mg of D-mannitol per 1 mg of a human monoclonal antibody.

There is no particular limitation on human monoclonal antibodies capable of being stabilized according to this invention, and various human monoclonal antibodies can be used. For example, CLN-IgG, SLN-IgG, CoLN-IgA, TOS/H8-IgM [Hideaki Hagiwara : BIOINDUSTRY, 4, 730 (1987)], etc. can be exemplified as representative examples.

Such a human monoclonal antibody can be made into preparations for putting to practical use as medicinal drugs, etc. As a process for making into a preparation, there can, for example, be mentioned a process which comprises, according to necessity, concentrating a purified human monoclonal antibody by ultrafiltration, sodium sulfate fractionation or the like, substituting a buffer solution suitable for the preparation by a gel filtration method, in some case further adjusting the concentration, making a filtration sterilization processing, and then making freeze drying.

In preparation of a stabilized human monoclonal antibody preparation, it is possible to compound D-mannitol as a stabilizer at any stage of the above making of a preparation, but generally, it is suitable to introduce D-mannitol into a human monoclonal antibody preparation by a dialytic method after substitution with a buffer solution suitable for a preparation by a gel filtration method. The concentration of D-mannitol in a D-mannitol solution usable for the dialytic method differs depending on the concentration of a human monoclonal antibody solution to be dialyzed, and for example is suitable in the range of generally 0.1 to 2% (w/v), preferably 0.5 to 1.5% (w/v) in case the concentration of the human monoclonal antibody is 1 mg/ml, and suitable in the range of generally 0.1 to 10% (w/v), preferably 0.5 to 5% (w/v) in case the concentration of the human monoclonal antibody is 5 mg/ml.

The content of D-mannitol can be in the range of 1 to 20 mg, preferably 5 to 15 mg per 1 mg of the human monoclonal antibody in the preparation. When the content of D-mannitol is smaller than 1 mg, a desired sufficient stabilization effect cannot be obtained, and when it is larger than 20 mg, agglutination of the antibody comes conversely to be observed.

Further, it was revealed that stability of the preparation was further enhanced by using glycine in addition to D-mannitol. Although the use quantity of glycine at that time is not strictly restricted, but it is suitable that the use quantity is in the range of generally 0.005 to 0.2 millimole, preferably 0.1 to 0.15 millimole per 1 mg of the human monoclonal antibody.

Introduction of glycine into the preparation of this invention can be made at the same time of introduction of D-mannitol.

Further if necessary, it is possible to compound a suitable quantity of a phosphate salt or the like for adjustment of pH into the preparation of this invention.

EXAMPLE

This invention is further specifically described below according to examples.

Reference Example 1
Preparation of Human Monoclonal Antibody

Frozen cells of an antibody producing cell [human×human hybridoma=CLN H11 (ATCC HB 8307 deposited on May 20, 1983, with the American Type Culture Collection (ATCC), whose address is 10801 University Blvd., Manassas, Va. 20110-2209, under the terms of the Budapest Treaty.)] were thawed, and the thawed cells were washed with a basal medium and then cultured using a basal medium containing 10% fetal bovine serum. After culture, the cells were taken from this culture broth and cultured again in a serum-free medium (Hybrity-II, produced by HIH Biocenter Co. located at Kasai-shi, Hyogo-ken, Japan), and then scale up was made by batch culture in the same medium. Cells were removed from 40 liters of the resultant serum-free culture broth, and the resultant solution was concentrated to about 5 liters by ultrafiltration (PROSTAK™, produced by Millipore Co.).

Salting-out was carried out by adding ammonium sulfate to the concentrate so that the final concentration of the saturated solution became 70% to obtain a precipitate with ammonium sulfate.

This ammonium sulfate precipitate was dialyzed twice against 20 liters each of 10 mM phosphate buffer solution (hereafter referred to as PB) for total 24 hours, and then adsorbed on a cation exchange column (S-Sepharose™, fast flow, produced by Pharmacia Co.). The column adsorbate was sufficiently washed with 10 mM PB, and then eluted by an NaCl concentration gradient from 0 to 0.5 M in 10 mM PB to obtain a rough fraction of IgG.

This was adsorbed on a Protein A column (produced by Repligen Co.), and after sufficient washing with 10 mM PB+1 M NaCl, eluted with 0.1 M glycine-hydrochloric acid+1M NaCl (pH 3.0).

The resultant IgG was concentrated by ammonium sulfate fractionation (saturation concentration 50%), and the concentrate was subjected to gel filtration using a Sephacryl S-300™ column (produced by Pharmacia Co.) equilibrated with 10 mM phosphate-buffered physiological saline (hereafter referred to as PBS) to obtain purified IgG.

Reference Example 2
Preparation of Stabilizer, Etc.
(1) The phosphate-buffered physiological saline (PBS) was prepared by dissolving 1.15 g of $Na_2HPO_4$ (anhydrous), 8.0 g of NaCl, 0.2 g of $KH_2PO_4$ and 0.2 g of KCl in about 900 ml of distilled water, adjusting the pH to 7.2 to 7.4, and making the total quantity 1.0 liter.
(2) As the physiological saline for injection was used one produced by Otsuka Pharmaceu tical Co.
(3) The mannitol solutions were prepared by diluting 20% (w/v) D-mannitol injection produced by Otsuka Pharmaceutical Co. with distilled water to concentrations of 1%, 5% and 10% (w/v), respectively.
(4) 1% mannitol+physiological saline for injection was prepared by dissolving D-mannitol in physiological saline for injection to make the concentration 1% (w/v).
(5) The glycine-mannitol solution was prepared by dissolving 22.5 g of glycine, 50 ml of 20% D-mannitol solution and 1.56 g of $NaH_2PO_4 \cdot 2H_2O$ in about 900 ml of water and adjusting the pH to 7.2 to 7.4, and making the total quantity 1.0 liter.

Example 1
Preparation and Stability of Freeze Dried Agents of a Human Monoclonal Antibody—(1)

The human monoclonal antibody solution prepared in Reference example 1 was dialyzed against each solution prepared in Reference example 2. The resultant each human monoclonal antibody solution was adjusted to each concentration of 1.0, 2.5 and 5.0 mg/ml. The resultant solutions were passed through a membrane filter of 0.22 μm, and 1 ml portions thereof were poured into vials and freeze dried using a tray dryer produced by LABCONCO Co., USA. Freeze drying was made by holding the samples at a shelf temperature of −30° C. for about three hour for freezing, and after complete freezing of the samples, starting drying by moving a suction pump. The shelf temperature was raised to 0° C., and about 20 hours later, the freeze drying was finished.

1 ml portions of distilled water were added to the vials, respectively to dissolve freeze dried powders, and solubilities were compared based on $OD_{600}$ values usually used in measurement of the turbidity of culture broths of bacteria, etc. When insoluble particles were formed as a result of aggregation of the antibody, etc., $OD_{600}$ values increase. As a result, it was revealed, as shown in the following Table 1, that the 1% (w/v) mannitol solution and the glycine-mannitol solution are the best in view of solubility after freeze drying of the human monoclonal antibody. Further, even in case of the solutions of mannitol alone, the solubility went bad in the solutions having high concentrations of 5% and 10% (w/v). Further, even when the concentration of mannitol was 1% (w/v), existence in 0.9% or so of NaCl made the solubility worse, as shown in the result of 1% mannitol+physiological saline for injection.

TABLE 1

Solubility ($OD_{600}$) of human monoclonal antibody after freeze drying in each stabilizer

| Stabilizer | Quantity (mg) of antibody in one vial | | | |
|---|---|---|---|---|
| | 0 | 1.0 | 2.5 | 5.0 |
| PBS | 0.019 | 0.194 | 0.311 | 0.427 |
| Physiological saline for injection | 0.001 | 0.220 | 0.582 | 0.952 |
| 1% mannitol | 0.001 | 0.014 | 0.035 | — |
| 5% mannitol | 0.000 | 0.194 | 0.270 | — |
| 10% mannitol | 0.001 | 0.246 | 0.317 | — |
| 1% mannitol + physiological saline for injection | 0.001 | 0.193 | 0.228 | — |
| Glycine-mannitol | 0.010 | 0.042 | — | 0.115 |

Example 2
Preparation and Stability of Freeze Dried Agents of a Human Monoclonal Antibody—(2)

According to the method described in Example 1, freeze dried agents were prepared containing in one vial 1, 2, 5, 10, 15, 20, 50 or 100 mg of D-mannitol and 1, 2.5 or 5 mg of the monoclonal antibody, and solubilities were compared. The results are shown in Table 2.

As a result, it was revealed that when the quantity of D-mannitol after freeze drying is in the range of 1 to 20 mg per 1 mg of the antibody, sufficient solubility can be obtained.

TABLE 2

Solubility ($OD_{600}$) of human monoclonal antibody after freeze drying in D-mannitol

| Quantity (mg) of D-mannitol one vial | Quantity (mg) of antibody in one vial | | |
|---|---|---|---|
| | 1 mg | 2.5 mg | 5 mg |
| 1 | 0.007 | 0.008 | 0.008 |
| 2 | 0.005 | 0.004 | 0.013 |
| 5 | 0.003 | 0.003 | 0.002 |
| 10 | 0.001 | 0.004 | 0.008 |
| 15 | 0.002 | 0.002 | 0.005 |

TABLE 2-continued

Solubility (OD$_{600}$) of human monoclonal antibody after freeze drying in D-mannitol

| Quantity (mg) of D-mannitol one vial | Quantity (mg) of antibody in one vial | | |
|---|---|---|---|
| | 1 mg | 2.5 mg | 5 mg |
| 20 | 0.005 | 0.012 | 0.006 |
| 50 | 0.194 | 0.022 | 0.024 |
| 100 | 0.246 | 0.127 | 0.031 |

Industrial Applicability

As stated above, the human monoclonal antibody preparation of this invention is excellent in stability in a solution state, a freeze drying state and a freezing state, particulary stability against aggregation and precipitation of the human monoclonal antibody at the time of redissolution after freeze drying, and is useful as a medicinal drug.

What is claimed is:

1. A stabilized freeze-dried human monoclonal antibody composition comprising human monoclonal antibody produced by hybridoma cell line having ATCC accession number HB8307, from about 0.005 to 0.2 millimole of glycine per 1 mg of the human monoclonal antibody, from about 1 to 20 mg of D-mannitol per 1 mg of the human monoclonal antibody, and an amount of pH stabilizing phosphate salt to stabilize the pH of the composition in the range of from about pH 7.2 to pH 7.4.

2. A process for stabilizing a human monoclonal antibody composition produced by hybridoma cell line having accession number HB8307, which comprises dialyzing the human monoclonal antibody in a phosphate salt stabilized buffer solution having a pH in the range of from about 7.2 to about 7.4, said solution comprising from about 1 to about 20 mg of D-mannitol per mg of said monoclonal antibody, from about 0.005 to 0.2 millimole of glycine per mg of said monoclonal antibody, and an amount of pH stabilizing phosphate salt to stabilize the pH of said solution.

* * * * *